United States Patent
Fukuda et al.

(10) Patent No.: US 7,067,157 B2
(45) Date of Patent: Jun. 27, 2006

(54) FLAKY α-ALUMINA PARTICLES AND METHOD FOR PRODUCING THE SAME

(75) Inventors: Takeshi Fukuda, Kurobe (JP); Ryuichi Shido, Kurobe (JP)

(73) Assignee: Kinsei Matec Co., Ltd., Osaka (JP)

( * ) Notice: Subject to any disclaimer, the term of this patent is extended or adjusted under 35 U.S.C. 154(b) by 0 days.

(21) Appl. No.: 09/834,651

(22) Filed: Apr. 16, 2001

(65) Prior Publication Data

US 2001/0043910 A1 Nov. 22, 2001

(30) Foreign Application Priority Data

Apr. 17, 2000 (JP) .................................. 2000-114625
Feb. 16, 2001 (JP) .................................. 2001-040237

(51) Int. Cl.
*A01N 59/06* (2006.01)
*A61K 33/06* (2006.01)

(52) U.S. Cl. ..................... 424/682; 424/401; 424/489; 423/625

(58) Field of Classification Search ................ 424/401, 424/489, 682; 423/625
See application file for complete search history.

(56) References Cited

U.S. PATENT DOCUMENTS

| | | | |
|---|---|---|---|
| 5,401,703 A | * | 3/1995 | Fukuda ..................... 501/153 |
| 5,587,010 A | | 12/1996 | Shibasaki et al. |
| 6,015,456 A | * | 1/2000 | Fukuda et al. ........... 106/186.5 |
| 6,080,380 A | | 6/2000 | Shibasaki et al. |
| 6,197,277 B1 | * | 3/2001 | Fukuda et al. .............. 423/628 |

FOREIGN PATENT DOCUMENTS

| | | |
|---|---|---|
| EP | 0 522 519 A2 | 1/1993 |
| EP | 0 761 600 A1 | 3/1997 |
| JP | 35-6977 | 10/1957 |
| JP | 9 227337 | 9/1997 |
| WO | WO 92/19536 | 11/1992 |

* cited by examiner

*Primary Examiner*—Sreeni Padmanabhan
*Assistant Examiner*—Shobha Kantamneni
(74) *Attorney, Agent, or Firm*—Finnegan, Henderson, Farabow, Garrett & Dunner, L.L.P.

(57) ABSTRACT

Flake-like α-alumina particles having an average major diameter of 0.5 to 25 μm and an aspect ratio, expressed by particle major diameter/average thickness, of greater than 50 to 2000 and having a thin flat form. The flake-like α-alumina particles are produced by a hydrothermal synthesis process of an aqueous slurry in which the slurry comprises an alumina hydrate and/or an alumina gel, having a particle size of not more than 2 μm and a maximum size of not more than 5.0 μm and phosphoric acid ions in an amount of $1.0 \times 10^{-3}$ to $1.0 \times 10^{-1}$ mol per mol of the alumina hydrate and/or alumina gel. The flake-like α-alumina particles exhibit good dispersibility when being kneaded as fillers or pigments in rubbers or plastics or as coating agents with a resin and also can be easily dispersed as primary particles in aqueous solvent with high dispersion stability when added to an aqueous slurry of precision abrasives or cosmetics. The particles are desirable in providing cosmetics with good smoothness, tackiness to the skin and spreadability.

6 Claims, 1 Drawing Sheet

FLAKY α-ALUMINA PARTICLES AND METHOD FOR PRODUCING THE SAME

BACKGROUND OF THE INVENTION

The present invention relates to flake-like α-alumina particles having a very high aspect ratio which exhibit good dispersibility when being kneaded as fillers or pigments in rubbers or plastics or as coating agents, with a resin and which can be easily dispersed as primary particles in aqueous solvent with high dispersion stability and desirable orientation when added to an aqueous slurry of precision abrasives or cosmetics. The present invention also relates to a method for producing such flake-like α-alumina particles. Further, the present invention relates to a cosmetic containing the flake-like α-alumina particles, and more particularly a cosmetic that has a good tackiness to the skin and a pleasant smoothness in use, covers spots and freckles, and provides a suitable gloss and luster and a transparency that does not darken.

Known methods for producing plate-like alumina particles by using, as a starting raw material, alumina gel obtained by neutralization of aluminum hydroxide or aluminum ions obtained by Bayer's process etc., include a calcination process comprising addition of a mineralizer as disclosed in Japanese Patent Publication No. 35-6977. However, the particles processed by such a known method contain a large proportion of aggregated flaky particles and when added to a resin component, an improved mechanical strength of the resin component or a feeling of gloss can hardly be obtained.

In view of the foregoing, there was proposed a method for producing plate-like particles having a uniform particle shape and good dispersibility by conducting a hydrothermal treatment on an aqueous slurry of aluminum hydroxide in an autoclave and the obtained particles exhibited an improved dispersibility when kneaded with a resin component (Japanese Patent Publication 5-17132A). However, when these plate-like particles are added to an aqueous solvent to be used in a slurry form of precision abrasives or cosmetics, even such improved alumina powder cannot smoothly advance dispersion in the solvent and tends to cause re-aggregation of particles once dispersed in the solvent. As a result, such alumina particles still have problems or difficulties in reducing the surface roughness of an article to be polished or in providing a cosmetic powder with a sufficient spreadability and a capability to develop gloss after application, etc.

In order to give a fine texture and improved mechanical physical properties to molded final products and to improve the stability of a coating film and a slurry as well as the gloss of a dried product after application, flake-like particles are required to have dispersibility in a resin component or various solvents. In order to meet such requirements, the particles have to be insusceptible to aggregation and have affinity to the dispersing medium and the surface state of electrically charged particles have to be in a desirable state.

Especially, when the conventional flake-like particles are used in cosmetics, further problems have been encountered. Pigments that have been added to conventional cosmetics include talc, mica, kaolin, sericite, and other extender pigments, titanium dioxide, zinc oxide, and other white pigments, iron oxide, chromium oxide, ultramarine, Prussian blue, and other coloring pigments, and, if needed, titanium oxide fines and other such ultraviolet shielding pigments or titanium, mica, and other such sheen agents.

An extender pigment has a poor hiding power because its refractive index is close to that of oils used in combination, but is added because it improves the feel of a cosmetic (how well it adheres and spreads and how smooth it makes the skin feel) and enhances moldability. White pigments generally do have hiding power because of their large refractive index, and are added in order to cover up spots, freckles, and the like on the skin when the cosmetic is applied.

Coloring pigments impart a color to the skin, and are added in order to give a healthy and attractive appearance. Ultraviolet shielding agents, sheen agents, and the like are also added as needed.

These various pigments are mixed as dictated by the intended use of the cosmetic, and the cosmetic is produced by suitably adding higher aliphatic alcohols, higher fatty acids, ester oils, paraffin oils, waxes, and other such oil components, ethyl alcohol, propylene glycol, sorbitol, glucose, and other such alcohols, mucopolysaccharides, collagens, lactates, and other such humectants, various surfactants, thickeners, antioxidants, pH buffers, preservatives, perfumes, and so forth.

When various pigments are compounded in a cosmetic, talc, mica, kaolin, sericite, and other such extender pigments are generally in the form of flake particles of silicates that are found in nature. This shape is what provides smoothness, tackiness and spreadability when the cosmetic is applied to the skin, but because these natural products contain coloring components such as iron as impurities, the oils contained in the cosmetic or perspiration from the skin can decrease the transparency of the cosmetic over time, resulting in what is known as "darkening."

At the same time, another important characteristic that is required of an extender pigment is that it impart gloss or luster that has the look of natural transparency, so that the made-up skin looks fresher. Crushed mica and the like have been used in recent years in an attempt to meet this requirement, but the luster and gloss thereof are greatly affected by the flake-like particle thickness and the smoothness of the particle surface, and with a crushed material, particle smoothness is lost and a luster and gloss having the look of natural transparency are not achieved.

Titanium dioxide, which is the most commonly used white pigment, has a very high refractive index, and therefore it scatters light very well and has good hiding power. However, with a cosmetic containing a large proportion of a pigment with such a high refractive index, the hiding power is actually too high, which can give a feeling of a thick makeup, so that the makeup cannot be finished with a natural feeling. Titanium dioxide also generally tends to aggregate, and has a high coefficient of friction, so another drawback to its use is that smoothness and other such aspects of usage feel deteriorate.

BRIEF SUMMARY OF THE INVENTION

Therefore, the object of the present invention is to provide flake-like alumina particles which have a thin flattened form and such a good orientation as to retain a stable dispersion state in an aqueous solvent, while maintaining a uniform shape, which is characteristic of alumina particles produced by hydrothermal synthesis, and dispersibility in the state of primary particles. As a result of diligent research aimed at solving the above problems, the inventors arrived at the present invention upon discovering that the above problems can be solved by using such specific flake-like α-alumina particles in various applications as mentioned above.

This invention are as follows:

(1) Flake-like α-alumina particles having an average major diameter of 0.5 to 25 μm and an aspect ratio, expressed by particle major diameter/particle thickness, of greater than 50 (excluding 50) to 2000 and having a thin flat form.

(2) The flake-like α-alumina particles described in the above item (1), wherein a phosphoric compound is present in an amount of 0.2 to 5.0% by weight, in terms of oxide $P_2O_5$, relative to the weight of the alumina particles.

(3) The flake-like α-alumina particles described in the above item (1) or (2), wherein the isoelectric point of the alumina particles at which zeta-potential is 0 is at a pH of 4 to 8.

The method for producing the above-mentioned flake-like α-alumina particles are as follows:

(4) A method for producing the flake-like α-alumina particles described in any one of the above items (1) to (3), comprising a hydrothermal synthesis process of an aqueous slurry in which the aqueous slurry comprises an alumina hydrate and/or an alumina gel, having a particle size regulated to not more than 2 μm in average particle size and not more than 5.0 μm in maximum particle size, as a starting raw material, and phosphoric acid ions are added in an amount of $1.0 \times 10^{-3}$ to $1.0 \times 10^{-1}$ mol per mol of the alumina hydrate and/or alumina gel as the starting raw material.

(5) The method for producing the flake-like α-alumina particles described in the above item (4), in which besides the alumina hydrate and/or alumina gel as the starting raw material and the phosphoric acid ions, α-alumina particles having an particle major diameter of less than 1 μm and a specific surface area of at least 5 $m^2/g$ are further added in an amount of $1.0 \times 10^{-6}$ to $5.0 \times 10^{-3}$ mol per mole of the alumina hydrate and/or alumina gel as the starting material for conducting the hydrothermal synthesis process, so that the resultant flake-like α-alumina particles are controlled in particle major diameter.

The present invention also provides the following cosmetic that provides a good tackiness to the skin and a pleasant smoothness in use, covers spots and freckles, and gives a suitable gloss and luster as well as a transparency that does not darken.

(6) A cosmetic containing flake-like α-alumina particles described in any one of the above item (1) to (3).

(7) The cosmetic according to the above item (6), in which the flake-like α-alumina particles have an average thickness of 0.01 to 0.1 μm and an average particle diameter, in terms of half the sum of particle diameter in major axis and particle diameter in minor axis, of 0.5 to 15 μm.

(8) A cosmetic containing flake-like α-alumina particles having an average thickness of 0.01 to 0.1 μm and an average particle diameter, in terms of half the sum of particle diameter in major axis and particle diameter in minor axis, of 0.5 to 15 μm.

(9) The cosmetic described in any one of the above items (6) to (8), in which the flake-like α-alumina particles are compounded in an amount of 1 to 90% by weight based on the weight of the cosmetic.

The form of the flake-like α-alumina produced in this invention are as shown in FIG. 1. An α-alumina particle produced by a conventional hydrothermal synthesis process is formed of faces n, c, a, r, etc., as shown in FIG. 2. However, the flake-like particle of this invention is constituted of only faces n and c. Throughout the specification, the "particle major diameter" or "major diameter" is used to mean the diameter in the major axis of the face c and the aspect ratio is expressed by a ratio of (major diameter in the face c)/(thickness L expressed by two opposite faces c) unless otherwise specified. These values are determined from the arithmetical means of the values measured for ten particles arbitrarily selected by scanning electron microscope observation. In some case of using the flake-like α-alumina particles in cosmetics, the diameter of the flake-like α-alumina particles is expressed by the arithmetical mean of the values of (diameter in major axis+diameter in minor axis)/2 for ten particles as arbitrarily selected above. The particle diameter thus obtained is referred merely to "particle diameter" in order to distinguish the above (particle) major diameter. The particle size of the alumina hydrate and alumina gel used for the synthesis of the flake-like α-alumina particles is expressed by the particles size measured in a manner commonly used in the art unless otherwise specified.

DETAILED DESCRIPTION OF THE INVENTION

Figure 1:
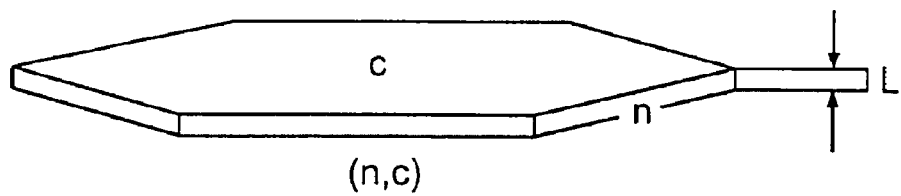
FIG. 1 is a view illustrating of the configuration of the flake-like particle produced by this invention.
Figure 2:
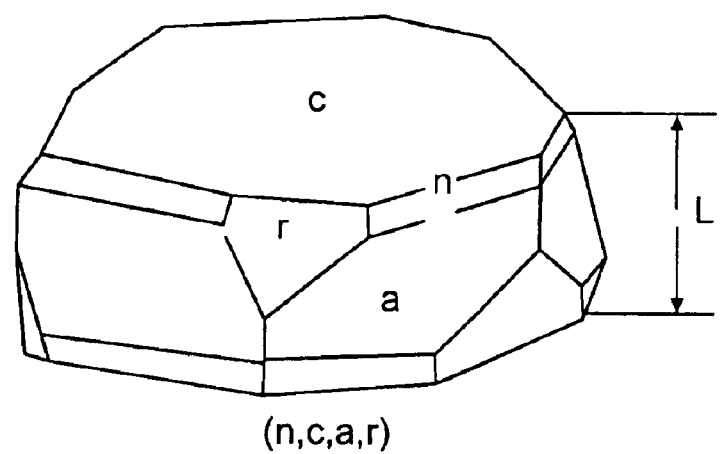
FIG. 2 a view illustrating the configuration of the plate-like particle produced by a conventional hydrothermal synthesis process.

The present invention will now be described in detail.

The particle major diameter of the flake-like α-alumina particles is 0.5 μm to 25 μm and preferably 2 μm to 20 μm, whereas the thickness is small. Therefore, the particles has a large aspect ratio of more than 50(not including 50) to 2000, preferably more than 50(not including 50) to 200, more preferably 55 to 200 and most preferably 60 to 200. The thickness is in the range meeting the above requirements and desirably in the range of 0.01 μm to 0.2 μm.

In order to obtain flake-like α-alumina particles which can achieve the objects of this invention, their average particle major diameter and the aspect ratio are key features and therefore they should be within the above specified ranges. Further, the above-specified preferred ranges are effective in enhancing the effects, especially with respect to the orientation of the particles.

In this invention, there is no particular restriction on the alumina hydrate and alumna gel used as the raw material. Gibbsite-type aluminum hydroxide obtained by Bayer's process, alumina hydrate such as boehmite or alumina gel prepared from amorphous aluminum hydroxide, alumina hydrate or the like can be used. Throughout the specification, the term "raw material" or "starting raw material" used to prepare an aqueous slurry means alumina hydrate or alumina gel of aluminum compounds, unless otherwise specified.

The raw material are preferably adjusted in particle size to have an average particle size of 2 μm or less with a maximum particle size being 5 μm or less. Preferably, the average particle size is within 0.1 to 1.5 μm. Excessive pulverization, by which the particle size of the raw material becomes less than 0.1 μm, provides particles having too small a particle major diameter after hydrothermal synthesis and accordingly the aspect ratio becomes small. Furthermore, the use of raw material particles having a very small particle size tends to produce too small particle product. Therefore, aggregation of synthesized particles tends to occur and dispersion in the sate of primary particles in a resin component or an aqueous solvent is not successfully advanced. When the raw material having a maximum particle size over 5 μm is used, the flake-like particles obtained by hydrothermal synthesis include strongly aggregated secondary particles and dispersibility cannot be improved.

A ball mill or medium stirrer mill is usually used for adjusting the particle size of the raw material powder but the method for the particle size adjustment is not limited only to such methods.

In accordance with the present invention, a slurry prepared by mixing the above-mentioned raw material with water is subjected to a hydrothermal synthesis treatment. The concentration of the raw material in the slurry is 1 to 60% by weight and preferably 20 to 50% by weight. A concentration exceeding 60% by weight will increase the possibility of occurrence of the aggregation of particles.

Increasing the addition of phosphoric acid ions within the range of $1.0 \times 10^{-3}$ to $1.0 \times 10^{-1}$ per mol of the starting raw material (alumina hydrate and/or alumina gel) is effective in providing a small thickness and a large aspect ratio to the resultant flake-like particles. The phosphoric acid ions are usually added as an aqueous solution of orthophosphoric acid, metaphosphoric acid or pyrophosphoric acid. However, the source material for phosphoric acid ions is not necessarily restricted to these phosphoric acids. Examples of the source materials which introduce phosphoric acid ions include phosphonic acid or phosphinic acid or various phosphates such as dihydrogenphosphate sodium or other phosphates of alkali metal (sodium, potassium, etc.), ammonium phosphate or other phosphates. Also, any of various condensed phosphates may be used, such as hexametaphosphate or orthometaphosphate obtained by the dehydration condensation of the above. When the addition of phosphoric acid ions is under $1.0 \times 10^{-3}$ mol per mol of the starting raw material, the flake-like particles synthesized become thick and the synthesis of particles having an aspect ratio of more than 50 becomes difficult. On the other hand, an addition of phosphoric acid ions exceeding $1.0 \times 10^{-1}$ mol per mole of the starting raw material, a large amount of flake-like particles made by hydrothermal synthesis process turn to aggregated secondary particles.

As an effective method to control the average particle major diameter of the flake-like particles, addition of α-alumina particles, having an particle major diameter of less than 1 μm and a specific surface area of at least 5 m$^2$/g, as seed crystals to the slurry prepared from a mixture of the raw material and water is effective. The addition of the seed crystals to the slurry is desirably effected by dispersing using, for instance, an ultrasonic disperser, etc. Addition in such a manner makes the synthesized flake-like alumina particles finer with an increase in the addition amount of the seed crystals. Addition of seed crystals having a particle major diameter of 1 μm or more increases the proportion of particles having a thickness of 0.2 μm or more and makes it difficult to synthesize desired flake-like particles. Addition of seed crystals having a specific surface area of less than 5 m$^2$/g makes the particle size control difficult. The seed crystals are preferably added in an amount of $1.0 \times 10^{-6}$ to $5.0 \times 10^{-3}$ mol per mol of the starting raw material. Addition exceeding $5.0 \times 10^{-3}$ mol diminishes the effect of making the particle major diameter fine. Owing to the addition of the above seed crystals, the resultant flake-like α-alumina particles can have a particle major diameter controlled within the range of 0.5 to 25 μm.

The temperature for the hydrothermal synthesis process is at least 350° C., and preferably 450° C. or higher. In the case where the slurry temperature reaches, at highest, 400 to 450° C., at least 24 hours are needed to complete the conversion reaction to α-alumina after the temperature of the slurry is heated to the reaction temperature. The pressure for the hydrothermal synthesis is preferably 5 MPa to 25 MPa, and preferably 7.5 MPa to 20 MPa. The relationship between the temperature and the pressure for the hydrothermal synthesis should be within the range of α-Al$_2$O$_3$ (corundum) in an Al$_2$O$_3$—H$_2$O system phase diagram. The reason why the hydrothermal synthesis pressure of at least 5 MPa is that under a pressure lower than this pressure the particles are synthesized in a mixed state of flake-like particles and granular particles and the distribution of the particle major diameters becomes broad. Further, when the pressure exceeds 20 MPa, the resultant particles tend to have a large thickness. A pressure exceeding 25 MPa is unfavorable because the thickness of the particles become too large.

In accordance with the present invention, there can be synthesized flake-like α-alumina particles having an average major diameter of 0.5 to 25 μm and an aspect ratio of greater than 50(excluding 50) to 2000. In this invention, the average particle major diameter can easily control within the above-mentioned range by controlling the amount of added seed crystals.

The flake-like particles obtained by the invention contain few aggregated particles, and when they are kneaded as a filler into a plastic and rubber, the flake-like particles establish a good dispersion state in the resultant composite material because of their specific flake shape. Furthermore, when this composite composed of the resin component and the particles as a filler is formed into a sheet form, the tensile strength, stiffness and other mechanical strength of the sheet are improved because of high degree of flatness of the particles. Furthermore, shrinkage which occurs due to a fall in temperature after forming into a desired form is small.

Moreover, when the particles are used as pigments for paints or as coating agents and coating films are formed, the particles are oriented in parallel in the coating films. Therefore, degradation of the coating films is prevented and the effect of preventing the invasion of corrosive substances inside the coating films can be expected. Since no projection of the particles on the surface of the coating films is detected, the coating films have an outstanding surface smoothness and show a desirable glossiness.

As a further advantageous feature of the particles, affinity with an aqueous solvent is also good, and the particles can establish a stable dispersion state of primary particles by conducting a simple dispersion operation. Therefore, when the particles are dispersed in an aqueous solvent for applications to slurries of precision abrasives or cosmetics, improvements in the surface smoothness of articles to be polished or the stability and spreadability of liquid cosmetics can be expected. The reason for good dispersibility of the alumina particles of the present invention in an aqueous solvent or medium has not been elucidated. However, most important factor is that they are in the form of specific flake-like α-alumina particles having the above-specified average particle major diameter as well as the specified aspect ratio. Also, it is presumed to be one of the important factors that since the flake-like α-alumina particles may comprise a phosphoric compound in an amount of 0.2 to 5.0% by weight, in terms of oxide P$_2$O$_5$, relative to the weight of the alumina particles, phosphoric acid ions can be present on the surface of the particles when dispersed in an aqueous solvent and further since the particle surface is charged a little, expulsive force works between particles. The term "phosphoric compound" means the compound or compounds resulting from the compound or compounds added as the source material for the phosphoric acid ions in the slurry and exist on the hydrothermally synthesized flake-like α-alumina particles. The amount of such phosphoric compound(s) is indicated in terms of oxide, i.e., $P_2O_5$. A further feature is that due to the presence of phosphoric ions on the surface of the flake-like particles, the particles have an isoelectric point in a pH range different from the pH range of 8 to 9 of the isoelectric point in the case of conventional alumina particles.

Hereinafter, the cosmetics of the present invention will be specifically described. In the cosmetics, the above-mentioned flake-like α-alumina particles have an average thickness preferably in the range of 0.01 to 0.1 μm, more preferably in the range of 0.05 to less than 0.1 μm, and an average particle diameter preferably in the range of 0.5 to 15 μm, more preferably in the range of 1.0 to 10 μm. In some case, cosmetics can contain flake-like α-alumina particles having two essential features, i.e., an average thickness of 0.01 to 0.1 μm and an average particle diameter of 0.5 to 15 μm and such cosmetics are included within the present invention.

If the average thickness exceeds 0.1 μm, some difficulties may arise in imparting high quality luster or gloss with a natural transparent feeling. In particular, if the edges of the flake particles are thick, this tends to cause scattering reflection of light, which will impair luster or gloss with a transparent look. On the other hand, if the average thickness is less than 0.01 μm, crumbling of the particles tends to occur in the course of producing the cosmetic product, making it difficult for the flakes to keep their shape, and once again it will be difficult to obtain luster or gloss with a transparent look.

If the average particle diameter is over 15 μm, the cosmetic will feel rough on the skin and be unpleasant to use. If the average particle diameter is less than 0.5 μm, tackiness to the skin will be good, but spreadability and smoothness cannot be easily obtained.

The amount in which the flake-like α-alumina particles are compounded into the cosmetic is preferably 1 to 90% by weight, and more preferably 5 to 60% by weight. It is undesirable to exceed 90% by weight because the moldability of the cosmetic will be poor and the gloss and luster will be excessive. At less than 1% by weight, there will be a reduction in smoothness and tackiness to the skin, it will be difficult to obtain luster or gloss with a transparent look, and the "darkening" encountered with conventional extender pigments will tend to occur.

The flake-like α-alumina particles of the present invention can be used in any application desired, such as in foundation, lipstick, eye shadow, mascara, and other makeup cosmetics, or in milky lotions, creams and other facial cosmetics.

The flake-like α-alumina particles used in cosmetics are produced as follows, for example.

The flake-like particles are produced by subjecting the raw material aluminum hydroxide or alumina hydrate to a hydrothermal treatment in the presence of phosphoric acid ions. A specific producing method is described below, but the present invention is not limited to this.

The starting raw material, namely, aluminum hydroxide or an alumina hydrate such as boehmite, is first ground in a ball mill, an agitation medium mill, or the like and adjusted in particle size to obtain raw material particles with a particle size of 0.1 to 5.0 μm, and preferably 0.3 to 3.0 μm.

It is generally preferable for the phosphoric acid ions to be added as a phosphoric acid aqueous solution and the compounds as having been mentioned as the source material for phosphoric acid ions can be used.

The above-mentioned additives are added in a range such that there will be $3.0 \times 10^{-3}$ to $2.5 \times 10^{-2}$ mol, and preferably $5.0 \times 10^{-3}$ to $1.2 \times 10^{-2}$ mol, as phosphoric acid ions, per mol of the raw material such as aluminum hydroxide.

In the hydrothermal synthesis treatment, a 50% by weight slurry containing the above-mentioned starting raw material in an amount of 50% by weight based on the weight of the slurry and additives mixed with water was prepared, this slurry is put into a pressure vessel, and the raw material is subjected to a hydrothermal synthesis treatment at a synthesis temperature of at least 350° C., and preferably between 450 and 600° C., at a synthesis pressure of 5 to 20 MPa, and preferably between 7.5 and 15 MPa, and at a temperature elevation rate of 50° C./minute to 0.3° C./minute until α-alumina particles are produced.

For example, the above-mentioned producing method will yield flake-like α-alumina particles with an average thickness of 0.01 to 0.1 μm and an average particle diameter of 0.5 to 15 μm.

In addition to the above-mentioned flake-like α-alumina particles, raw materials that are ordinarily used in cosmetics, such as higher aliphatic alcohols, higher fatty acids, ester oils, paraffin oils, waxes, and other such oil components, ethyl alcohol, propylene glycol, sorbitol, glucose, and other such alcohols, mucopolysaccharides, collagens, lactates, and other such humectants, various surfactants, thickeners, antioxidants, pH buffers, preservatives, perfumes, and so forth, are suitably selected and compounded into the cosmetic of the present invention.

The present invention will now be described in further detail through examples, but the present invention is not limited to or by these examples.

EXAMPLE 1

Aluminum hydroxide of gibbsite type obtained by Bayer's process s was adjusted to an average particle size of 1.1 μm. To the thus obtained raw material, orthophosphoric acid was added in an amount of $3.0 \times 10^{-3}$ mol per mol of the raw material to form an aqueous slurry containing the raw material in a concentration of 50% by weight. Hydrothermal synthesis was performed on the slurry at a synthesis temperature of 600° C. and a synthesis pressure of 15 MPa and the product was washed with water and dried. Thus, a white powder was obtained.

The powder was composed of flake-like α-alumina particles having an average particle major diameter of 12.0 μm and an average thickness of 0.15 μm and an aspect ratio of 80. It was confirmed by analysis of the composition of the powder by fluorescence X-ray that the powder contained 0.3% by weight of $P_2O_5$ in terms of oxide. The isoelectric point was at pH 5.8.

The particles obtained above were added to a resin component (Experiment 1) and an aqueous solvent (Experiment 2), respectively to evaluate the dispersibility for the respective additions.

Experiment 1: To 100 parts of the particles, 50 parts of an acrylic lacquer (produced by Mizutani Paint), 20 parts of toluene and 10 parts of methyl ethyl ketone were added, and stirred by a homogenizer (LR-41B made by ika, 1000 rpm) for 5 minutes to form a slurry. After applying the resultant slurry onto a glass plate, the applied sample was dried by being heated for 1 hour at 50° C. to form a hardened product.

Experiment 2: 40 parts of pure water was added to 100 parts of the particles, and stirred by a homogenizer (LR-41B made by ika, 1000 rpm) for 5 minutes to form a slurry. After applying the resultant slurry onto a glass plate, the applied sample was dried by being heated for 30 seconds at 120° C. to form a hardened product.

Each sample on the glass plate was subjected to analysis by X-ray diffraction and the degree of orientation was calculated by the Lotgering method. The higher the dispersibility, the greater the degree of orientation becomes toward 1. The degree of orientation in Experiment 1(dispersion in resin) was 0.91, while the degree of orientation in Experiment 2(dispersion in an aqueous solvent) was 0.84.

EXAMPLE 2

A white powder was obtained by hydrothermal synthesis as described in Example 1, except that the addition amount of orthophosphoric acid was increased to $1.0 \times 10^{-2}$ mol per mol of the raw material.

The powder was composed of flake-like α-alumina particles having an average particle major diameter of 11.0 μm and an average thickness of 0.07 μm and an aspect ratio of about 160. It was confirmed by analysis of the composition of the powder that the powder contained 0.9% by weight of $P_2O_5$ in terms of oxide. The isoelectric point was at pH 5.3. The degree of orientation in the above Experiment 1 (addition in resin) was 0.90 and the degree of orientation in the above Experiment 2(addition in aqueous solvent) was 0.88.

EXAMPLE 3

A white powder was obtained by hydrothermal synthesis as described in Example 2, except that, in the aqueous slurry, besides orthophosphoric acid, α-alumina particles having a particle major diameter of 0.1 μm and a specific surface area, measured by the BET method, of 14 $m^2/g$(manufactured by Taimei Kagaku Kogyo K.K., TM-DAR) were further added as seed crystals in an amount of $8.0 \times 10^{-6}$ mol per mol of the raw material.

The powder was composed of flake-like α-alumina particles having an average particle major diameter of 7.5 μm and an average thickness of 0.05 μm and an aspect ratio of 150. It was confirmed by analysis of the composition of the powder that the powder contained 0.8% by weight of $P_2O_5$, in terms of oxide. The isoelectric point was at pH 5.6. The degree of orientation in the above Experiment 1(addition in resin) was 0.88 and the degree of orientation in the above Experiment 2(addition in aqueous solvent) was 0.82.

EXAMPLE 4

A white powder was obtained by hydrothermal synthesis as described in Example 2, except that in the aqueous slurry, besides orthophosphoric acid, α-alumina particles having a particle major diameter of 0.1 μm and a specific surface area, measured by the BET method, of 14 $m^2/g$(manufactured by Taimei Kagaku Kogyo K.K., TM-DAR) were further added as seed crystals in an amount of $8.0 \times 10^{-5}$ mol per mol of the raw material.

The powder was composed of flake-like α-alumina particles having an average particle major diameter of 4.8 μm and an average thickness of 0.04 μm and an aspect ratio of 120. It was confirmed by analysis of the composition of the powder that the powder contained 0.8% by weight of $P_2O_5$ in terms of oxide. The isoelectric point was at pH 6.0. The degree of orientation in the above Experiment 1 (addition in resin) was 0.89 and the degree of orientation in the above Experiment 2 (addition in aqueous solvent) was 0.81.

In the above Examples 1–4, the raw material adjusted in particle size had an maximum particle size of not greater than 5 μm.

COMPARATIVE EXAMPLE 1

The procedure as described in Example 1 was carried out, except that the average particle size of the raw material was adjust to 4.0 μm and hydrothermal synthesis was conducted without addition of orthophosphoric acid. The product was washed and dried to obtain a white powder.

The powder was composed of plate-like particles having an average particle major diameter of 5.0 μm and an average thickness of 0.75 μm and an aspect ratio of about 7. It was confirmed by analysis of the composition of the powder that the powder contained no $P_2O_5$ as oxide. The isoelectric point was at pH 8.5. The degree of orientation in the above Experiment 1(addition in resin) was 0.42 and the degree of orientation in the above Experiment 2(addition in aqueous solvent) was 0.39.

COMPARATIVE EXAMPLE 2

Hydrothermal synthesis was performed as described in Example 2 except that α-alumina particles having a particle major diameter of 2.0 μm and a specific surface area of 15 $m^2/g$ were added as seed crystals in an amount of $8.0 \times 10^{-5}$ per mol of the raw material in the slurry and a white powder was obtained.

The powder was composed of particles having an average particle major diameter of 10.5 μm and an average thickness of 0.30 μm and an aspect ratio of 35. It was confirmed by analysis of the composition of the powder that the powder contained 0.8% by weight of $P_2O_5$ in terms of oxide. The isoelectric point was at pH 5.2. The degree of orientation in the above Experiment 1(addition in resin) was 0.60 and the degree of orientation in the above Experiment 2(addition in aqueous solvent) was 0.43.

The synthesis conditions of the above various powders are shown in Table 1 and the particle configuration, composition and degree of orientation as an indicator of the dispersibility for each powder are shown in Table 2.

TABLE 1

| | Synthesis Conditions | | | | |
| --- | --- | --- | --- | --- | --- |
| | | Amount of | Seed Crystals | | |
| | Particle size of raw material (μm) | $H_3PO_4$ addition (mol/1 mol of raw material) | Particle major diameter (μm) | Specific surface area ($m^2/g$) | Amount of addition (mol/1 mol of raw material) |
| Example 1 | 1.1 | $3.0 \times 10^{-3}$ | No addition of seed crystals | | |
| Example 2 | 1.1 | $1.0 \times 10^{-2}$ | No addition of seed crystals | | |
| Example 3 | 1.1 | $1.0 \times 10^{-2}$ | 0.1 | 14 | $8.0 \times 10^{-6}$ |
| Example 4 | 1.1 | $1.0 \times 10^{-2}$ | 0.1 | 14 | $8.0 \times 10^{-5}$ |
| Comparative Example 1 | 4.0 | No addition of $H_3PO_4$ | No addition of seed crystals | | |
| Comparative Example 2 | 1.1 | $1.0 \times 10^{-2}$ | 2.0 | 1.5 | $8.0 \times 10^{-5}$ |

TABLE 2

| | Configuration of particles | | | | Composition Content as $P_2O_5$ | Degree of orientation* | |
|---|---|---|---|---|---|---|---|
| | Average particle major diameter (μm) | Average thickness (μm) | Aspect ratio | Isoelectric point pH | (% by weight) | 1) | 2) |
| Example 1 | 12.0 | 0.15 | 80 | 5.8 | 0.3 | 0.91 | 0.84 |
| Example 2 | 11.0 | 0.07 | 160 | 5.3 | 0.9 | 0.90 | 0.88 |
| Example 3 | 7.5 | 0.05 | 150 | 5.6 | 0.8 | 0.88 | 0.82 |
| Example 4 | 4.8 | 0.04 | 120 | 6.0 | 0.8 | 0.89 | 0.81 |
| Comparative Example 1 | 5.0 | 0.75 | 7 | 8.5 | 0 | 0.42 | 0.39 |
| Comparative Example 2 | 10.5 | 0.30 | 35 | 5.2 | 0.8 | 0.60 | 0.43 |

*1): Experiment of addition in resin
2): Experiment of addition in aqueous solvent

EXAMPLE 5 AND COMPARATIVE EXAMPLES 3 AND 4

[Production Example of Flake-like α-Alumina Particles]

Aluminum hydroxide as a starting raw material was first ground in a ball mill, etc. and adjusted to a particle size of 1.0 μm. This product was mixed with water to produce a 50% by weight slurry containing the raw material particles in an amount of 50% by weight based on the weight of the slurry. Sodium phosphate was added to this slurry to give as phosphoric acid ions in an amount of $5.0 \times 10^{-3}$ mol per mol of aluminum hydroxide, and was thoroughly mixed and dissolved.

A pressure vessel was filled with the above-mentioned raw material, and the temperature was raised to 600° C. at a rate of 1.6° C./minute in an electric furnace, after which the material was held for 3 hours at 600° C., 7.5 MPa. After the vessel had cooled, the product was washed with pure water, filtration was fully conducted, and the product was dried for 12 hours in a 100° C. dryer to obtain a white powder.

The powder thus obtained was subjected to powder X-ray diffraction, which revealed only a diffraction peak for α-alumina. The particles were also observed under an electron microscope, which revealed them to be flake-like particles with an average particle diameter of 2.5 μm, an average thickness of 0.05 μm, and an aspect ratio (half of the arithmetical sum of diameter in major axis and diameter in minor axis to thickness) of 50 which gave greater than 50 when converted to another aspect ratio of particle diameter in major axis to thickness.

[Production Example of Ordinary Granular α-Alumina Particles]

The starting raw material (aluminum hydroxide with an average particle size of 25 μm) was put in an alumina vessel, the temperature was raised to 1300° C. at a rate of 3.3° C./minute in an electric furnace, and the product was held for 2 hours at 1300° C.

After the vessel had cooled, the product was washed with pure water, filtration was fully conducted, the product was ground for 4 hours in a wet ball mill to adjust the particle size, and then the particles were dried for 24 hours in a 100° C. dryer to obtain a white powder.

The powder thus obtained was subjected to powder X-ray diffraction, which revealed only a diffraction peak for α-alumina. These particles were also observed under an electron microscope, which revealed them to be granular or irregular-shaped particles with an average particle diameter of 3.0 μm.

The above powders were used to prepare powdery foundations with the composition shown in Table 3. Powder components (1), (2), (3), (4), (5), and (6) in Table 3 were mixed ahead of time in a Herschel mixer, and components (7), (8), and (9) were heated and melted and then uniformly mixed into the above mixed powder. Each resultant mixture was ground in a pulverizer, was press molded in a holder to obtain each powdery foundation. The blend amounts in the examples are weight percentages.

Next, the effect that these flake-like α-alumina particles have in a cosmetic will be illustrated through examples and comparative examples, in which evaluations were made for four categories (tackiness to the skin, smoothness, gloss, and transparency) by organoleptic tests using a panel of five experts.

The evaluation scores represent the average score of the five experts, with scores given from 1 to 5, with 5 being the best. The results were as follows.

TABLE 3

Examples of Powdery Foundations

| | Blend amount (%) | | |
|---|---|---|---|
| Component | Ex. 5 | Comp. Ex. 3 | Comp. Ex. 4 |
| (1) flake-like α-alumina powder obtained in production example | 50 | 0 | 0 |
| (2) granular alumina powder obtained in production example | 0 | 50 | 0 |
| (3) talc | 15 | 15 | 40 |
| (4) sericite | 15 | 15 | 40 |
| (5) iron oxide | 4 | 4 | 4 |
| (6) titanium dioxide | 6 | 6 | 6 |
| (7) squalane | 6 | 6 | 6 |
| (8) liquid paraffin | 2 | 2 | 2 |
| (9) sorbitol sesquioleate | 2 | 2 | 2 |
| Total | 100 | 100 | 100 |
| Evaluation: | | | |
| Tackiness | 4.6 | 3.4 | 4.4 |
| Smoothness | 4.8 | 2.8 | 4.6 |
| Luster or gloss | 4.8 | 3.0 | 3.8 |
| Transparency with no darkening | 4.8 | 4.4 | 3.2 |

The above powders were used to prepare oil foundations with the compositions shown in Table4. Powder components (1), (2), (3), (4), (5), and (6) in Table 4 were mixed ahead of time in a Herschel mixer. Components (7), (8), and (9) were melted at 80° C. and then the powders were gradually added to the resultant oil phase, after which this product was uniformly dispersed in a homomixer and cooled to room temperature. This mixture was charged into a metal holder to obtain an oil foundation. The blend amounts in the examples are weight percentages.

Next, the effect that these flake-like α-alumina particles have in a cosmetic will be illustrated through examples and comparative examples, in which evaluations were made for four categories (tackiness, smoothness, gloss, and transparency) by organoleptic tests using a panel of five experts.

The evaluation scores represent the average score of the five experts, with scores given from 1 to 5, with 5 being the best.

The results were as follows.

TABLE 4

Oil Foundations

|  | Blend amount (%) | | |
| --- | --- | --- | --- |
|  | Ex. 5 | Comp. Ex. 3 | Comp. Ex. 4 |
| Component |  |  |  |
| (1) flak-like α-alumina powder obtained in production example | 40 | 0 | 0 |
| (2) granular alumina powder obtained in production example | 0 | 40 | 0 |
| (3) talc | 5 | 5 | 25 |
| (4) kaolin | 5 | 5 | 25 |
| (5) iron oxide | 4 | 4 | 4 |
| (6) titanium dioxide | 5 | 5 | 5 |
| (7) isopropyl palmitate | 10 | 10 | 10 |
| (8) liquid paraffin | 25 | 25 | 25 |
| (9) microcrystalline wax | 6 | 6 | 6 |
| Total | 100 | 100 | 100 |
| Evaluation: |  |  |  |
| Tackiness | 4.6 | 3.2 | 4.6 |
| Smoothness | 4.8 | 3.0 | 4.6 |
| Luster or gloss | 4.8 | 3.0 | 4.0 |
| Transparency with no darkening | 4.8 | 4.4 | 3.2 |

As described above, the flake-like α-alumina particles of the present invention are ones having an average major diameter of 0.5 to 25 μm and an aspect ratio of greater than 50 (excluding 50) to 2000 and since they are flat and can maintain a stable dispersion state in an aqueous solvent while maintaining dispersibility in the state of primary particles, the orientation of dispersed particles can be improved.

Especially, the present invention can provide alumina particles which can be easily dispersed as primary particles and exhibit a good dispersibility owning to the effect of phosphoric acid ions not only when they are kneaded with resin, but also when they are added to an aqueous solvent. Plastics, rubbers, etc. in which the particles are kneaded as fillers are reinforced by the outstanding dispersibility of the particles. Moreover, when they are dispersed in various solvents for use as pigments in for paints, or as coating agents, their fluidity and applicability can be maintained since an increase in the viscosity of the paints are suppressed. After applying, the flake-like particles are oriented in parallel in the coating film. Therefore, deterioration of the coating film is prevented. The effect of preventing the invasion of corrosive substance, etc. inside the coating film can be expected. Moreover, the particles make it possible to obtain a glossy coating film having excellent surface flatness and smoothness. Further, a slurry of precision abrasives using the particles of the present invention provides an improved surface smoothness to an articles to be polished. Also, with the cosmetic obtained with the present invention, the smoothness of the surface and the shape of the compounded flake-like α-alumina particles result in good tackiness to the skin and good smoothness, spots or freckles on the skin are covered up because of the hiding power of the cosmetic, which is attributable to a suitable difference in the refractive index of α-alumina and the oil components, and because no undesirable coloring components are contained as in natural products, and because of the extremely thin flake particles with their smooth surface, the resulting cosmetic has suitable gloss and luster as well as a transparent look that is not darkened by perspiration or oil.

Moreover, according to the production method of the flake-like α-alumina particles of this invention, the flake-like α-alumina particles having a combination of the above-mentioned superior properties can be produced easily and efficiently.

What is claimed is:

1. A composition comprising Flaky α-alumina particles having an average major diameter of 2.0 to 25 μm, an average thickness of 0.01 to 0.2 μm, an aspect ratio, expressed by average major diameter/average thickness, of 55 to 2000, wherein the particles are produced by employing a source material that will introduce phosphate ions and will result in a phosphoric compound present in an amount of about 0.2% to about 5.0% by weight, relative to the weight of the alumina particles, wherein the weight of the phosphoric compound used is expressed by weight in terms of $P_2O_5$.

2. The composition according to claim 1, wherein an isoelectric point of the alumina particles at which zeta-potential is 0 is at a pH of 4 to 8.

3. A cosmetic composition comprising flaky α-alumina particles having an average major diameter of 2.0 to 25 μm, an average thickness of 0.01 to 0.2 μm, and an aspect ratio, expressed by average major diameter/average thickness, of 55 to 2000, wherein the particles are produced by employing a source material that will introduce phosphate ions and will result in a phosphoric compound present in an amount of about 0.2% to about 5.0% by weight, relative to the weight of the alumina particles, wherein the weight of the phosphoric compound used is expressed by weight in terms of $P_2O_5$.

4. The cosmetic composition according to claim 3, in which the flaky α-alumina particles have an average thickness of 0.01 to 0.1 μm and an average particle diameter, in terms of half of the sum of particle diameter in major axis and particle diameter in minor axis, of 0.5 to 15 μm.

5. The cosmetic composition according to claim 3, wherein the flaky α-alumina particles are present in an amount of 1% to 90% by weight, based on the weight of the cosmetic.

6. The cosmetic composition according to claim 3, wherein an isoelectric point of the alumina particles at which zeta-potential is 0 is at a pH of 4 to 8.

* * * * *

UNITED STATES PATENT AND TRADEMARK OFFICE
CERTIFICATE OF CORRECTION

PATENT NO. : 7,067,157 B2 Page 1 of 1
APPLICATION NO. : 09/834651
DATED : June 27, 2006
INVENTOR(S) : Takeshi Fukuda It is certified that error appears in the above-identified patent and that said Letters Patent is hereby corrected as shown below:

In claim 1, col. 14, line 25, "Flaky" should read -- flaky --.

In claim 4, col. 14, line 54, "0.5" should read -- 1.0 --.

Signed and Sealed this

Twenty-first Day of November, 2006

JON W. DUDAS
*Director of the United States Patent and Trademark Office*